(12) United States Patent
Dong et al.

(10) Patent No.: US 12,133,636 B2
(45) Date of Patent: Nov. 5, 2024

(54) ENDOSCOPE SYSTEM AND INTEGRATED DESIGN METHOD FOR ENDOSCOPE CAMERA OPTICAL SYSTEM

(71) Applicant: BEIJING FANXING GUANGDIAN MEDICAL TREATMENT EQUIPMENT CO., LTD., Beijing (CN)

(72) Inventors: Guoqing Dong, Beijing (CN); Yang Xiang, Changchun (CN); Qi Li, Songyuan (CN); Feng Gao, Chang Ling County (CN); Xu Ning, Changchun (CN)

(73) Assignee: Beijing Fanxing Guangdiang Medical Treatment Equipment Co, Ltd., Beijing (CN)

( * ) Notice: Subject to any disclaimer, the term of this patent is extended or adjusted under 35 U.S.C. 154(b) by 1003 days.

(21) Appl. No.: 16/647,222

(22) PCT Filed: Dec. 28, 2017

(86) PCT No.: PCT/CN2017/119501
§ 371 (c)(1),
(2) Date: Aug. 12, 2020

(87) PCT Pub. No.: WO2019/127245
PCT Pub. Date: Jul. 4, 2019

(65) Prior Publication Data
US 2020/0375440 A1    Dec. 3, 2020

(51) Int. Cl.
*A61B 1/00*    (2006.01)
*A61B 1/05*    (2006.01)
(Continued)

(52) U.S. Cl.
CPC ........... *A61B 1/05* (2013.01); *A61B 1/00045* (2013.01); *A61B 1/00174* (2013.01);
(Continued)

(58) Field of Classification Search
CPC ... A61B 1/05; A61B 1/00045; A61B 1/00174; A61B 1/055; A61B 1/053; A61B 1/04;
(Continued)

(56) References Cited

U.S. PATENT DOCUMENTS 4,905,082 A     2/1990  Nishigaki et al.
4,976,524 A  *  12/1990 Chiba ................ G02B 23/2423
                                                     359/728
(Continued)

FOREIGN PATENT DOCUMENTS

CN     101109827 A    1/2008
CN     101681013 A    3/2010
(Continued)

OTHER PUBLICATIONS

"F-number", Wikipedia, https://en.wikipedia.org/wiki/F-number, accessed online Aug. 22, 2023 (Year: 2023).*
(Continued)

*Primary Examiner* — Stephone B Allen
*Assistant Examiner* — Adam W Booher
(74) *Attorney, Agent, or Firm* — HSML P.C.

(57) ABSTRACT

The present disclosure provides an endoscope system and an integrated design method for an endoscope camera optical system. The endoscope system includes an object lens module, relay module, eye lens module, optical interface light path module, and digital ultra-high definition camera successively arranged along the light path direction, wherein an image formed by the object lens module is projected to the optical interface light path module in a non-parallel light
(Continued)

manner/divergent light manner after passing through the relay module and the eye lens module.

24 Claims, 5 Drawing Sheets

(51) Int. Cl.
    *A61B 1/055*     (2006.01)
    *G02B 23/24*     (2006.01)

(52) U.S. Cl.
    CPC ............ *A61B 1/055* (2013.01); *G02B 23/243* (2013.01); *G02B 23/2453* (2013.01); *G02B 23/2484* (2013.01)

(58) Field of Classification Search
    CPC .. A61B 1/00163; A61B 1/002; G02B 23/243; G02B 23/2453; G02B 23/2484
    See application file for complete search history.

(56) References Cited

U.S. PATENT DOCUMENTS

| | | | | |
|---|---|---|---|---|
| 5,005,957 A | * | 4/1991 | Kanamori | G02B 13/18 359/708 |
| 5,416,634 A | * | 5/1995 | Ning | G02B 23/243 385/119 |
| 6,069,651 A | * | 5/2000 | Tsuyuki | G02B 23/2423 348/75 |
| 2009/0318758 A1 | * | 12/2009 | Farr | A61B 90/53 600/112 |
| 2016/0174808 A1 | * | 6/2016 | Gu | A61B 1/0638 600/109 |
| 2017/0059878 A1 | * | 3/2017 | Moore | G02B 5/3058 |
| 2017/0209050 A1 | * | 7/2017 | Fengler | G01J 3/4406 |

FOREIGN PATENT DOCUMENTS

| | | |
|---|---|---|
| CN | 105511085 A | 4/2016 |
| CN | 107102433 A | 8/2017 |

OTHER PUBLICATIONS

"Effective Aperture and the Exit Pupil", https://coinimaging.com/effap_pupil.html, available at least as of Jul. 27, 2015, accessed online Aug. 23, 2023 (Year: 2015).*
PCT International Search Report, Application No. PCT/CN2017/119501, dated Mar. 15, 2018, 4 pages: with English translation.
Partial Supplementary European Search Report for EP Patent Application No. 17936800.6 dated Mar. 18, 2021; 12 pp.

* cited by examiner

ENDOSCOPE SYSTEM AND INTEGRATED DESIGN METHOD FOR ENDOSCOPE CAMERA OPTICAL SYSTEM

CROSS REFERENCE TO RELATED APPLICATIONS

This patent application is a National Stage Entry of PCT/CN2017/119501 filed on Dec. 28, 2017, the disclosure of which is incorporated by reference herein in its entirety as part of the present application.

BACKGROUND

The present disclosure relates to an endoscope optical system, and in particular to an integrated endoscope and a design method for an endoscope optical system.

With rapid development of science and technology, whether in the field of medical technology such as ear endoscope, nasal endoscope, laryngoscope, laparoscope, urinary system endoscope, gynecological endoscope, arthroscope and the like, or in the industrial field such as flaw detection endoscope, inspection endoscope and the like, the endoscopes has been used in more and more widespread manner. The existing endoscopes are used almost completely in combination with a camera system. From the original rigid endoscope camera of line 330, line 430, line 480 to 1920*1080P full high-definition (HD) camera system, and with the development from a CCD chip to a CMOS chip, the currently used CMOS chip has been able to reach the standard of 3840*2160 8 million pixel 4K ultra high-definition videotaping. However, the optical endoscope cannot reach the ultra-high-definition level due to limitations of the optical structure, which affecting the overall display effect of image.

BRIEF DESCRIPTION

In view of the technical problems in the related art, the present disclosure provides an endoscope system, which includes an object lens module, a relay module, an eye lens module, an optical interface light path module, and a digital ultra-high-definition camera, which are sequentially arranged along a light path direction, characterized in that an image formed by the object lens module is projected to the optical interface light path module in a form of non-parallel light/divergent light after passing through the relay module and the eye lens module.

According to the above described endoscope system, the endoscope is a rigid endoscope.

According to the above described endoscope system, the non-parallel light/divergent light forms a high-definition image on the digital camera after passing through the optical interface light path module.

According to the above described endoscope system, an imaging quality of the image formed on the digital ultra-high-definition camera is better than an imaging quality of an image output by the optical interface light path module.

According to the above described endoscope system, an imaging quality of the image formed on the digital camera is better than an imaging quality of an image formed on a visual plane of the eye lens module.

According to the above described endoscope system, a relative aperture of the system is W=D/f, where W is the relative aperture, D is an entrance pupil diameter of the entire system, i.e., an entrance pupil diameter of a visual system, and f is a combined focal length of the system; $f=(f_o \cdot f_C)/f_e$, where $f_o$ is a focal length of the object lens module, $f_C$ is a focal length of the optical interface light path module, and $f_e$ is a focal length of the eye lens.

According to the above described endoscope system, the relative aperture of the system of 1:4 to 1:6.

According to the above described endoscope system, an entrance pupil diameter of the object lens module for products of different specifications is about 0.2 mm to 1 mm.

According to the above described endoscope system, an exit pupil diameter of the eye lens module is about 3 mm-6 mm.

According to the above described endoscope system, an entrance pupil diameter of the object lens module is about 0.2 mm to 1 mm, and an exit pupil diameter of the eye lens module is about 3 mm to 6 mm.

According to the above described endoscope system, the system is used for a spherical or aspherical endoscope.

According to the above described endoscope system, the system is used for an endoscope having an appearance diameter of 1.9 mm, 2.7 mm, 4 mm, 5 mm, 6 mm, 8 mm, and 10 mm.

According to the above described endoscope system, a viewing-direction angle of the system may be 0°, 30°, 45°, or 70° or more.

According to the above described endoscope system, a distance from the object lens module to the eye lens module in the system may be of any length.

Another aspect of the present disclosure provides an integrated design method for an endoscope camera optical system, wherein the system includes an object lens module, a relay module, an eye lens module, an optical interface light path module, and a digital ultra-high-definition camera, which are sequentially arranged along a light path direction; a relative aperture of the system is increased by increasing an exit pupil diameter of the eye lens module so that a resolution of an image formed on the digital ultra-high-definition camera is improved.

According to the above described design method, the exit pupil diameter of the eye lens module is increased to about 3 mm-6 mm.

According to the above described design method, a resolution of the image formed on the digital camera is improved by increasing an entrance pupil diameter of the object lens module.

According to the above described design method, the entrance pupil diameter of the object lens module is increased to about 0.2 mm to 1 mm.

According to the above described design method, at the same time the exit pupil diameter of the eye lens module is increased to about 3 mm-6 mm, the entrance pupil diameter of the object lens module is increased to about 0.2 mm-1 mm.

According to the above described design method, a relative aperture of the system is W=D/f, where W is the relative aperture, D is an entrance pupil diameter of the entire system, i.e., an entrance pupil diameter of a visual system, and f is a combined focal length of the system; $f=(f_o \cdot f_C)/f_e$, where $f_o$ is a focal length of the object lens module, $f_C$ is a focal length of the optical interface light path module, and $f_e$ is a focal length of the eye lens.

According to the above described design method, the relative aperture of the system of 1:4 to 1:6.

According to the above described design method, the design method is used for a rigid endoscope.

According to the above described design method, the design method is used for a spherical or aspherical endoscope.

According to the above described design method, the system is used for an endoscope having an appearance diameter of 1.9 mm, 2.7 mm, 4 mm, 5 mm, 6 mm, 8 mm, and 10 mm.

According to the above described design method, a viewing-direction angle of the system may be 0°, 30°, 45°, or 70° or more.

According to the above described design method, a distance from the object lens module to the eye lens module in the system may be of any length.

Another aspect of the present disclosure provides an endoscope for the endoscope system as described above, wherein the endoscope includes the object lens module, the relay module, and the eye lens module.

Another aspect of the present disclosure provides an endoscope for the endoscope system as described above, wherein the endoscope includes the object lens module, the relay module, the eye lens module, and the optical interface light path module.

Another aspect of the present disclosure provides an optical adaptation interface for the endoscope system as described above, wherein the optical adaptation interface includes the optical interface light path module.

By increasing the entrance pupil diameter and exit pupil diameter of the endoscope optical system, the overall relative aperture is increased and the resolution is improved by the present disclosure. The overall optimization design of the endoscope system is considered as a whole without taking the image quality of each individual part into consideration.

BRIEF DESCRIPTION OF THE DRAWINGS

Hereinafter, example embodiments of the present disclosure will be further described in detail with reference to the accompanying drawings, in which.

DETAILED DESCRIPTION

In order that the technical solutions and advantages of the embodiments of the present disclosure will become clearer, technical solutions in the embodiments of the present disclosure will be described clearly and completely below in conjunction with the drawings in the embodiments of the present disclosure. Apparently, the described embodiments are some of the embodiments of the present disclosure, not all of them. All the other embodiments obtained by those skilled in the art based on the embodiments of the present disclosure without creative efforts will fall within the scope of the present disclosure.

In the following detailed description, reference may be made to various drawings which constitute a part of the present application and serve to explain the present application. In the drawings, similar reference signs denote substantially similar components in different figures. The individual specific embodiments of the present application will be described in sufficient detail below to enable those of ordinary knowledge and skills in the art to carry out the technical solutions of the present application. It is understood that other embodiments may be utilized, or structural, logical or electrical changes may be made to the embodiments of the present application.

The present disclosure provides a new integrated optical system of an endoscope, which can greatly improve the resolution of the endoscope. Moreover, in some embodiments of the present disclosure, the cost of the endoscope is not significantly increased.

Figure 1:
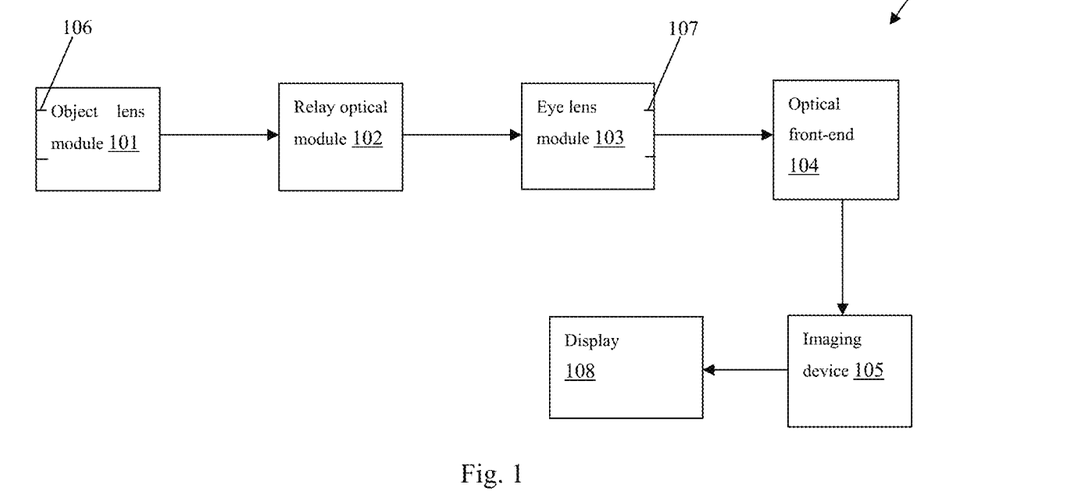
FIG. 1 is a schematic view of an endoscope optical system according to an embodiment of the present disclosure.

FIG. 1 is a schematic view of an endoscope optical system according to an embodiment of the present disclosure. As shown, the endoscope system 100 includes an object lens module 101, a relay module 102, an eye lens module 103, an optical interface light path module 104, and an imaging device 105. The imaging device 105 may be a digital ultra-high-definition camera. The object lens module 101 may include an entrance pupil 106 and a plurality of lenses for imaging an area to be observed. The entrance pupil 106 may be similar to a diaphragm and is configured to restrict light entering the object lens module. The relay module 102 includes a plurality of lenses for re-imaging light from an image formed by the object lens module for multiple times, thereby transmitting the image formed by the object lens module. The eye lens module 103 includes a plurality of lenses for magnifying an image received from the relay module 102. The eye lens module 103 includes an exit pupil 107. The optical interface light path module 104 includes a plurality of lenses for re-imaging light from an image formed by the eye lens module 103 onto an imaging surface of the imaging device 105. The optical interface light path module 104 is closely adjacent to the eye lens module 103, so the exit pupil 107 of the eye lens module 103 may also be used as an entrance pupil of the optical interface light path module 104. Further, the endoscope may include a display 108 for displaying an image from the imaging device 105.

Those skilled in the art should understand that the optical interface light path module 104 is adapted to the imaging device 105. In some embodiments, given the parameters of the optical interface light path module 104 and the imaging device 105, the optical system of the endoscope may include only the object lens module 101, the relay module 102, and the eye lens module 103. The designer designs the object lens module 101, the relay module 102, and the eye lens module 103 according to the parameters of the optical interface light path module 104 and the imaging device 105. Therefore, a situation in which the optical system of the endoscope does not include the optical interface light path module 104 and the imaging device 105 also falls within the scope of protection of the present disclosure. Further, in a case where the optical system of the endoscope may include only the object lens module 101, the relay module 102 and the eye lens module 103, given the imaging device 105, the designer may only design the optical interface light path module 104 and provide the optical interface light path module 104 separately. Therefore, the optical interface light path module 104 is also within the scope of protection of the present disclosure.

In the existing design of the endoscope optical system, the object lens module 102 and the relay module 103 are designed and tested as an entirety, and the eye lens module 104 is designed and tested separately. The optical interface light path module 104 is designed according to the exit pupil and field of view of the eye lens module 103 and to the imaging device 105 to ensure the imaging quality on the imaging surface of the imaging device 105. Those skilled in the art have tried for a long time with the hope of increasing the resolution of the endoscope and improving the quality of imaging by improving the design of the object lens module 102 and the relay module 103, the eye lens module 104 or the optical interface light path module 104, but no one succeeded.

In order to explain the structure of the endoscope optical system of the present disclosure, a new parameter is defined: overall relative aperture W, where $$W = D/f' \quad (1)$$

where W is a relative aperture, and D is an entrance pupil diameter of the optical system, which specifically may be the diameter of the entrance pupil 106 of the object lens module 101, and f' is a combined focal length of the optical system, which meets the following definition:

$$f' = (f'_O \cdot f'_C)/f'_e \quad (2)$$

where $f'_O$ is a focal length of the object lens module 101, $f'_C$ is a focal length of the optical interface light path module 104, and f'e is a focal length of the eye lens module 103.

For an optical system, the resolution can be determined by an image-side aperture angle (herein denoted by u'). Generally, the larger the image-side aperture angle is, the higher the resolution will be. The image-side aperture angle u' meets the following formula:

$$2 \tan u' = D_C/f'_C \quad (3)$$

where $D_C$ is an entrance pupil of the optical interface light path module 104, and $f'_C$ is a focal length of the optical interface light path module 104. Since the entrance pupil 108 of the optical interface light path module 104 is the exit pupil D' of the entire endoscope optical system, the following formula is established:

$$D_c = D' \quad (4)$$

Then, the following formula can be obtained:

$$2 \tan u' = D'/f'_C \quad (5)$$

Due to reversibility of the light path, the optical system of the endoscope can be approximately deemed as an inverted telescope. Therefore, the following formula is established:

$$D'/f'_C = D/f' \quad (6)$$

Then, the following formula may be obtained:

$$2 \tan u' = D/f' \quad (7)$$

It can be seen that the larger the relative aperture W of the optical system is, the larger the image-side aperture angle u' will be, and then the higher the resolution of the optical system will be.

According to an embodiment of the present disclosure, the range of the overall relative aperture W is 1:4 to 1:6. For example, the diameter of the entrance pupil of an existing φ10 mm laparoscope product is generally 0.2 mm to 0.4 mm, the exit pupil diameter is 1 mm to 2 mm, and the relative aperture is 1:10. In an embodiment of the present disclosure, the entrance pupil diameter is changed to 0.6 mm, the exit pupil diameter is changed to 3 mm to 6 mm, and the relative aperture is then 1:4 to 1:6. After that, a definition of MTF>0.2@120 lp/mm (that is, 120 pairs of lines can be resolved per millimeter) within a range of full field-of-view can be realized for different products having a field-of-view angle of 500 to 120°.

Further, according to formula (1), increasing the entrance pupil 106 of the object lens module 101 of the optical system is advantageous for improving the resolution of the optical system. According to an embodiment of the present disclosure, the entrance pupil diameter of the object lens module for products of different specifications is 0.2 mm to 1 mm.

As described above, from the perspective of the optical system, the optical system of the endoscope can be approximately deemed as an inverted telescope. The exit pupil D' of the eye lens module 103 meets the following formula:

$$D' = D \cdot f'_e / f'_o \quad (8)$$

where D' is the exit pupil diameter of the optical system, D is the entrance pupil diameter of the optical system, $f'_o$ is the focal length of the object lens module 101, $f'_C$ is the focal length of the optical interface light path module 104, and $f'_e$ is the focal length of the eye lens module 103.

With reference to formula (2), in case D is constant, the larger D' is, the larger $f'_e/f'_o$ will be. Typically, the focal length of the optical interface light path module 104 is constant, so the smaller $f' = (f'_o \cdot f'_C)/f'_e$ is, the larger W=D/f' will be.

Therefore, increasing the exit pupil diameter D' of the optical system (i.e., the exit pupil diameter of the eye lens module) is advantageous for improving the resolution of the system.

According to an embodiment of the present disclosure, the exit pupil diameter of the eye lens module is 3 mm to 6 mm.

According to an embodiment of the present disclosure, the sizes of the entrance pupil 106 and the exit pupil 107 have an influence on the resolution of the optical system of the endoscope. However, if the entrance pupil or the exit pupil is too large, too much stray light is introduced and the definition and resolution of the image will also be affected. According to an embodiment of the present disclosure, the entrance pupil diameter of the object lens module is 0.2 mm to 1 mm, and the exit pupil diameter of the eye lens module is 3 mm to 6 mm.

From the above description, it can be seen that the present disclosure obviates the shortcomings of separate design of the object lens module 102 and the relay module 103, the eye lens module 104, or the optical interface light path module 104, and adopts an integrated design concept to fully consider the reversibility of the light path, which can greatly improve the resolution of the endoscope. In some embodiments of the present disclosure, the definition of an endoscope using the optical system of the present disclosure can reach MTF>0.2@120 lp/mm, and the optical system of the present disclosure adds substantially no cost, thereby solving the problem of improving the resolution of the endoscope in the field that has not been addressed for a long time.

Further, the solution of the present disclosure does not affect other aspects of the optical system of the endoscope. According to an embodiment of the present disclosure, the optical system of the endoscope is used for a spherical or aspherical endoscope. According to an embodiment of the present disclosure, the optical system of the endoscope is used for an endoscope having an appearance diameter of 1.9 mm, 2.7 mm, 4 mm, 5 mm, 6 mm, 8 mm, and 10 mm. According to an embodiment of the present disclosure, the viewing-direction angle of the optical system of the endoscope may be 0°, 30°, 45°, or 70° or more. According to an embodiment of the present disclosure, a distance from the object lens module to the eye lens module in the optical system of the endoscope may be of any length.

In the following, the endoscope system with a viewing-direction angle of 30° according to an embodiment of the present disclosure will be described, and some comparisons will be made with existing endoscope optical systems to better illustrate the characteristics of the present disclosure. Those skilled in the art should understand that this embodiment is only used to explain the technical solution of the present disclosure and is not intended to limit the scope of the present disclosure.

Figure 2:
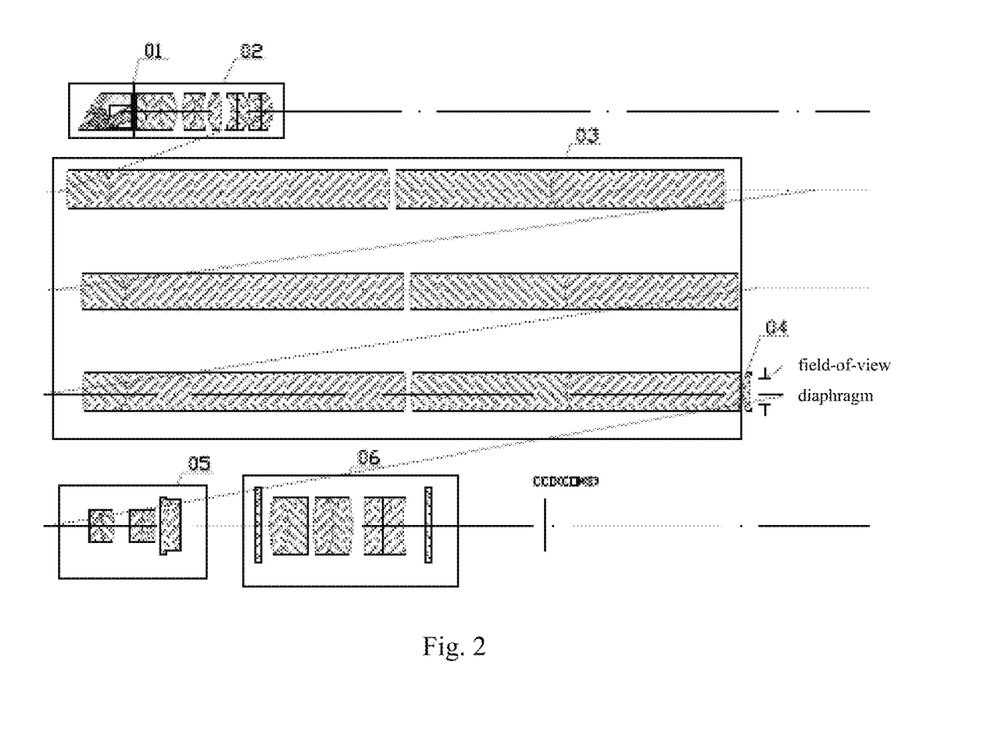
FIG. 2 is a schematic view of an endoscope optical system according to an embodiment of the present disclosure.
Figure 3:
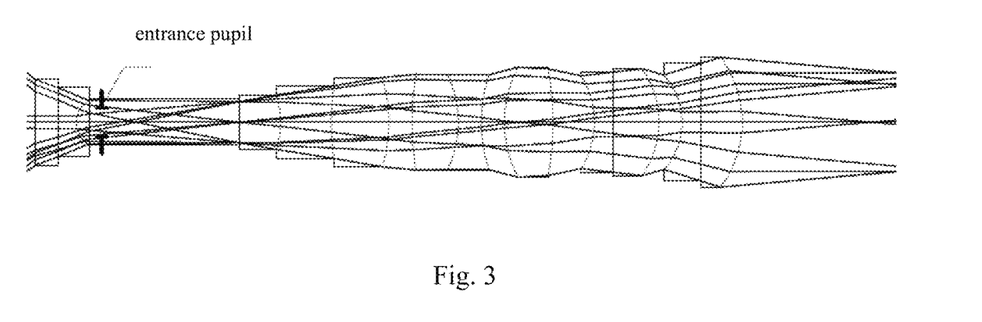
FIG. 3 is a schematic view of an object lens module of an endoscope optical system according to an embodiment of the present disclosure.
Figure 4:
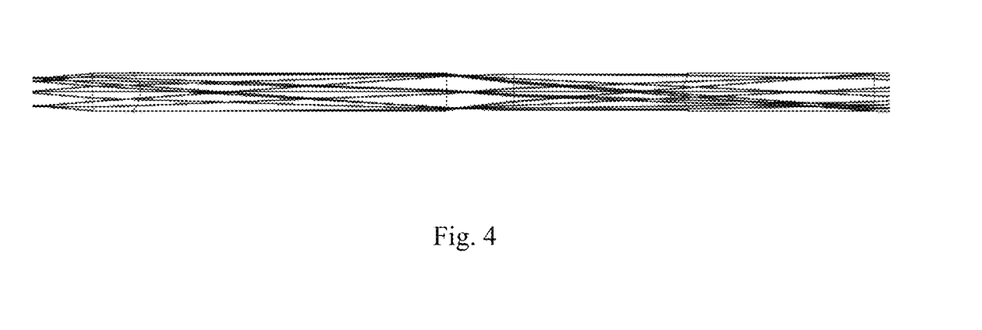
FIG. 4 is a schematic view of a relay module of an endoscope optical system according to an embodiment of the present disclosure.
Figure 5:
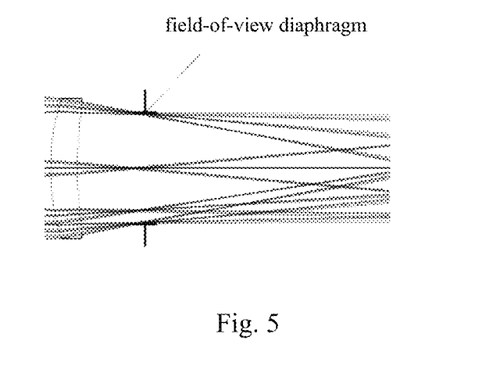
FIG. 5 is a schematic view of a field lens of an endoscope optical system according to an embodiment of the present disclosure.
Figure 6:
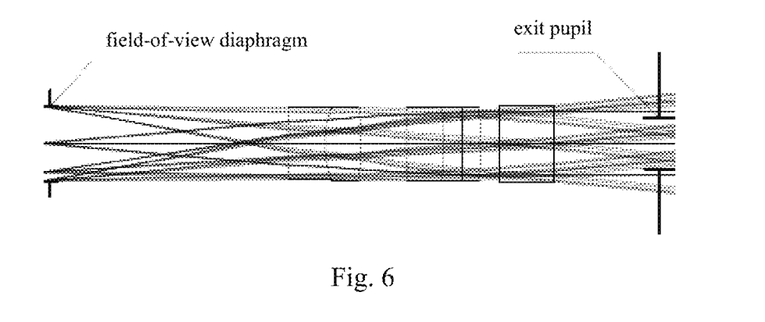
FIG. 6 is a schematic view of an eye lens of an endoscope optical system according to an embodiment of the present disclosure.
Figure 7:
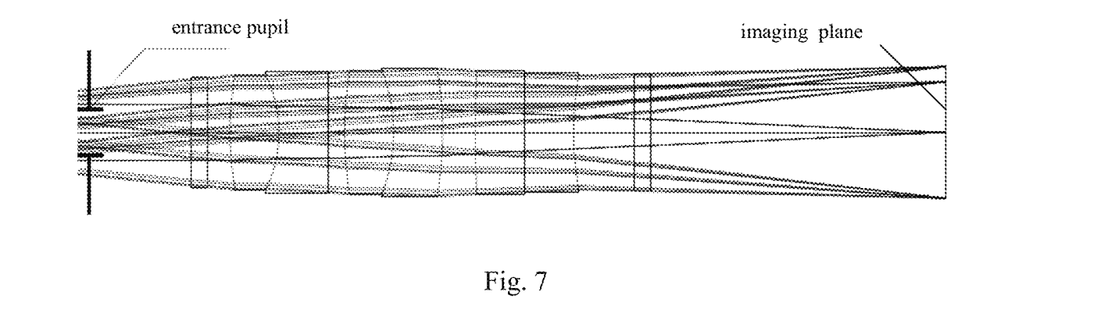
FIG. 7 is a schematic view of an optical interface light path module according to an embodiment of the present disclosure.

FIG. 2 is a schematic view of an endoscope optical system according to an embodiment of the present disclosure. FIG. 3 is a schematic view of an object lens module of an endoscope optical system according to an embodiment of the present disclosure. FIG. 4 is a schematic view of a relay module of an endoscope optical system according to an embodiment of the present disclosure. FIG. 5 is a schematic view of a field lens of an endoscope optical system according to an embodiment of the present disclosure. FIG. 6 is a schematic view of an eye lens of an endoscope optical system according to an embodiment of the present disclosure. FIG. 7 is a schematic view of an optical interface light path module according to an embodiment of the present disclosure.

The relative aperture of the existing endoscope is 1:8 to 1:10 and does not achieve a high-definition resolution. In this embodiment, the relative aperture is changed to 1:4.5, and a relative illuminance can reach 2 to 4 times of that of the existing endoscope. Specifically, the entrance pupil diameter of the existing endoscope is 0.2 mm to 0.4 mm, and the entrance pupil diameter of this embodiment is 0.6 mm. A 30° steering prism is unfolded into a flat plate, and the entrance pupil position is 2 mm behind a first negative lens. In this embodiment, the exit pupil diameter of the existing endoscope is 1 mm to 2 mm, the exit pupil diameter of this embodiment is 5 mm, and the exit pupil position is 4 mm behind the last lens of the eye lens module. In this embodiment, the entrance pupil diameter of the optical interface optical module is 5 mm, and the entrance pupil position is consistent with the exit pupil position of the eye lens module. In this embodiment, the endoscope can realize an observation direction with a viewing-direction angle of 30° and an observation range with a field-of-view angle of 70°.

Specifically, as shown in FIG. 2, the optical system of the endoscope includes an entrance pupil 01 of object lens module 02, a relay module 03, a field lens 04, a field-of-view diaphragm, an eye lens module 05, an optical interface light path module 06 and a CCD (CMOS) for imaging. FIG. 3 shows components of the object lens module and a light path therein. As shown, the object lens module 02 includes two monolithic lenses, one steering prism, one triple-glued lens, and three double-glued lenses. Through the object lens module of the optical system, the area to be observed can form a clear image after passing through the object lens module.

FIG. 4 shows a relay module and a light path therein. As shown, the relay module includes three identical image relay groups, and each image relay group includes two double-glued lenses. After multiple times of imaging by the relay module, the image formed by the object lens module is transmitted in the relay module. The relay module of the optical system of the present disclosure may include any number of image relay groups so that a distance from the object lens module to the eye lens module may be of any length.

FIG. 5 shows a field lens, a field-of-view diaphragm, and an associated light path. The field lens is disposed at a distance behind the last group of lenses of the relay module, and the image relay-transmitted is folded to reduce the aperture of the optical system of the eye lens module and the optical interface light path module. The diameter of the field-of-view diaphragm in this embodiment is 4.1 mm, and the size of the field of view is limited at 75°. FIG. 6 shows an eye lens module and a light path therein. As shown, the eye lens module includes two double-glued lenses. In this embodiment, the entrance pupil of the eye lens module has a diameter of 5 mm, and is disposed 4 mm behind the last group of lenses of the eye lens module. As shown in FIG. 6, the light emitted from the eye lens module is divergent/non-parallel, rather than parallel light. It is generally believed that the parallel light emitted by the eye lens module is a more reasonable choice. However, according to the optical system of the present disclosure, the light emitted from the eye lens module is non-parallel light, which will be more advantageous for improving the resolution of the endoscope optical system. FIG. 7 shows an optical interface light path module and a light path therein. As shown, the optical interface light path module includes three double-glued lenses. It should be noted that the exit pupil of the eye lens module in FIG. 6 is the entrance pupil of the optical interface light path module in FIG. 7. After passing through the optical interface light path module, the light from the eye lens module becomes a high-definition image on the imaging surface.

For a so-called high-definition image, it has a resolution of MTF>0.2@40 lp/mm or more, MTF>0.2@50 lp/mm or more, MTF>0.2@60 lp/mm or more, MTF>0.2@70 lp/mm or more, MTF>0.2@80 lp/mm or more, MTF>0.2@90 lp/mm or more, MTF>0.2@100 lp/mm or more, MTF>0.2@110 lp/mm or more, MTF>0.2@120 lp/mm or more, MTF>0.2@130 lp/mm or more, MTF>0.2@140 lp/mm or more, or MTF>0.2@150 lp/mm or more.

Figure 8:
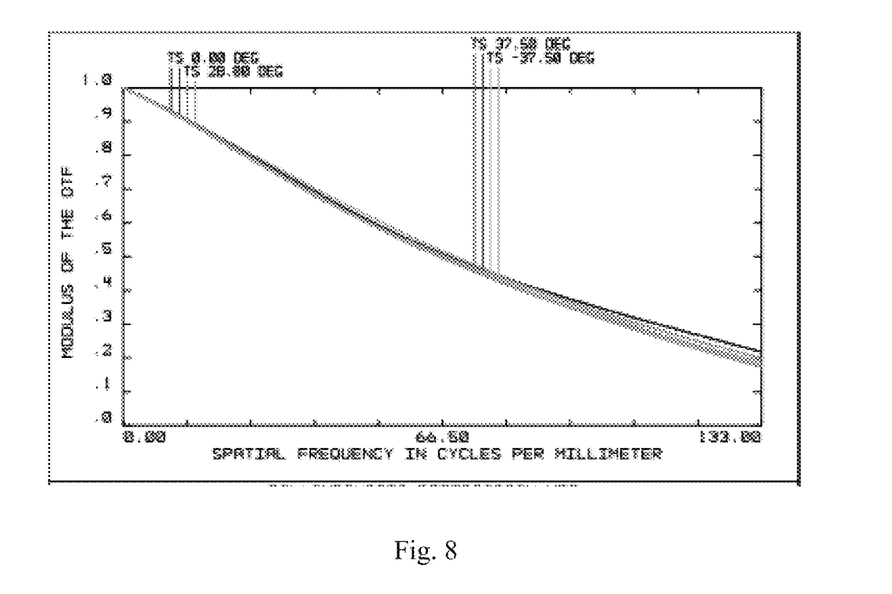
FIG. 8 is an MTF view of an endoscope system according to an embodiment of the present disclosure.
Figure 9:
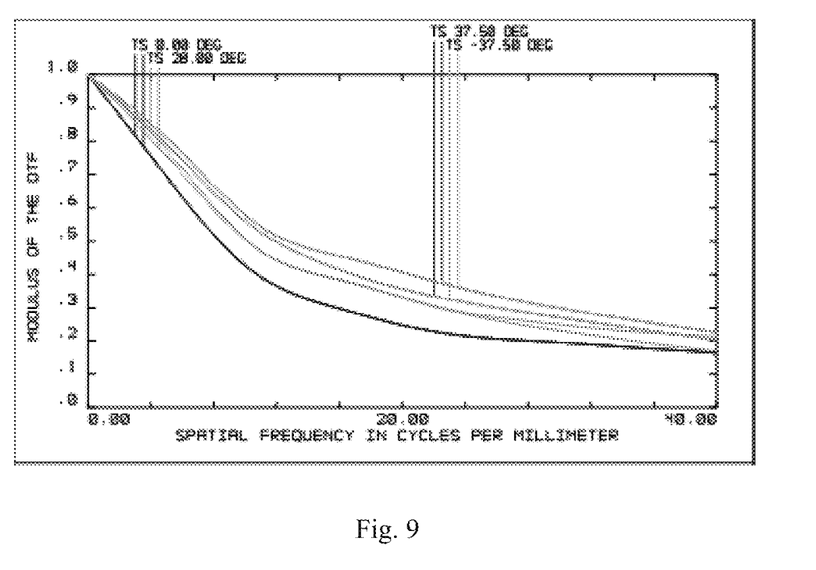
FIG. 9 is an overall MTF view of an object lens module and a relay module according to an embodiment of the present disclosure.
Figure 10:
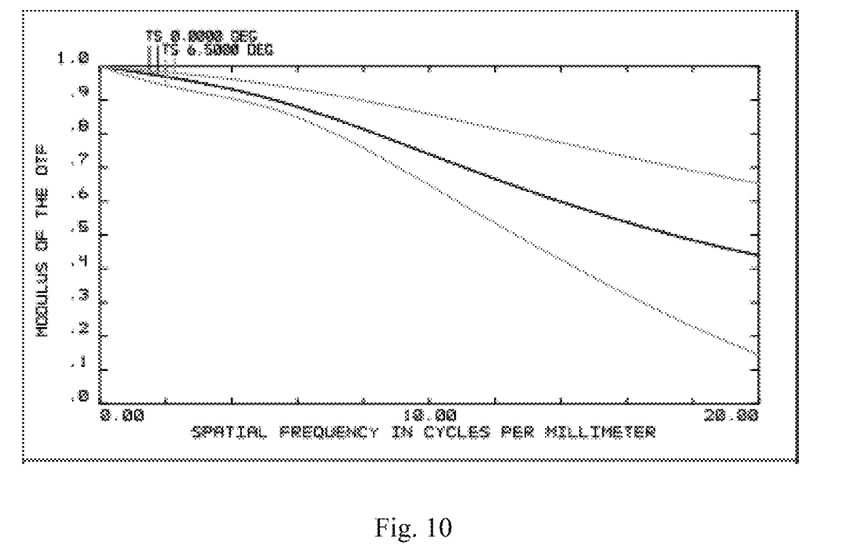
FIG. 10 is an MTF view of an eye lens according to an embodiment of the present disclosure.
Figure 11:
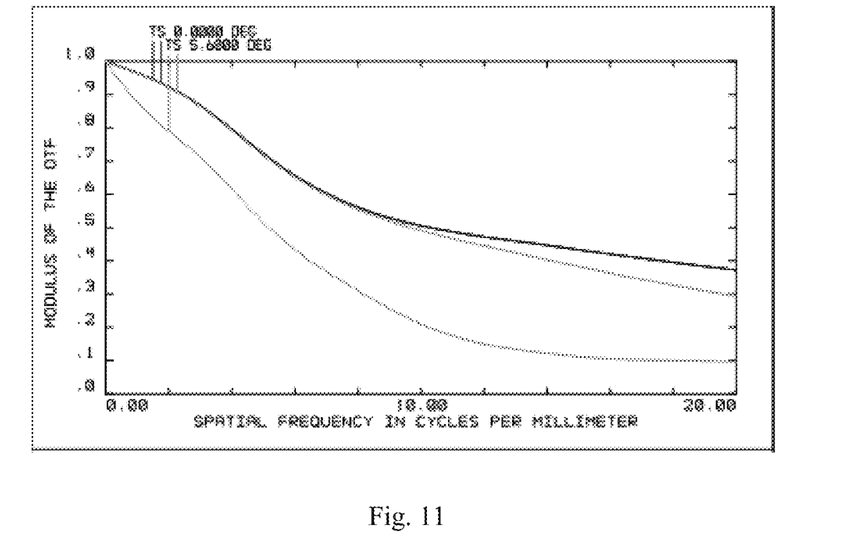
FIG. 11 is an optical MTF view of an optical interface according to an embodiment of the present disclosure.

FIG. 8 is an MTF view of an endoscope system according to an embodiment of the present disclosure. In this embodiment, the resolution of the optical system may be as high as MTF>0.2@120 lp/mm. Further, FIG. 9 is an overall MTF view of an object lens module and a relay module according to an embodiment of the present disclosure. FIG. 10 is an MTF view of an eye lens module according to an embodiment of the present disclosure. FIG. 11 is an optical MTF view of an optical interface according to an embodiment of the present disclosure.

It is worth noting that in this embodiment, referring to FIG. 9, the imaging quality of the object lens module lens only reaches MTF>0.2@40 lp/mm. In this embodiment, referring to FIG. 10, the imaging quality of the eye lens module only reaches MTF>0.2@20 lp/mm. However, in this embodiment, referring to FIG. 11, the imaging quality of the optical interface light path module has unexpectedly reached MTF>0.1@120 lp/mm. In other words, the imaging quality of the image formed on the imaging surface of the imaging device is better than the imaging quality of the image output by the object lens module and the relay optical group, or by the eye lens module, or by the optical interface light path module alone. The optical transfer function between the object lens module and the relay module, the eye lens module, and the optical interface light path module do not need to consider the imaging quality separately, but the overall optical transfer function (see FIG. 8) can meet the design requirements.

According to an embodiment of the present disclosure, an integrated design method for an endoscope optical system is provided. The design method may be applied to the optical system as described above. The optical system includes an object lens module, a relay module, and an eye lens module, which are sequentially arranged along a light path direction. The method includes increasing a relative aperture of the system by increasing an exit pupil diameter of the eye lens module, or increasing a relative aperture of the system by increasing an entrance pupil diameter of the object lens module. In some embodiments, the exit pupil diameter of the eye lens module is 3 mm to 6 mm. In other embodiments, the entrance pupil diameter of the object lens module is 0.2 mm to 1 mm.

According to an embodiment of the present disclosure, the relative aperture of the system may be increased by increasing the exit pupil diameter of the eye lens module and the entrance pupil diameter of the object lens module simultaneously. In some embodiments, the entrance pupil diameter of the object lens module is 0.2 mm to 1 mm, and the exit pupil diameter of the eye lens module is 3 mm to 6 mm.

Further, according to an embodiment of the present disclosure, the optical system further includes an optical interface light path module and an imaging device sequentially arranged along the light path direction, wherein the optical interface light path module is closely adjacent to the eye lens module. The method further includes setting the relative aperture of the system to 1:4 to 1:6, wherein the relative aperture of the system is W=D/f, where W is the relative aperture, D is an entrance pupil diameter of the optical system, and f is a combined focal length of the optical system, and $f=(f_o \cdot f_C)/f_e$, where $f_o$ is a focal length of the object lens module, $f_C$ is a focal length of the optical interface light path module, and $f_e$ is a focal length of the eye lens module.

According to an embodiment of the present disclosure, the system is used for a spherical or aspherical endoscope optical system. According to an embodiment of the present disclosure, the system is used for an endoscope optical system having an appearance diameter of 1.9 mm, 2.7 mm, 4 mm, 5 mm, 6 mm, 8 mm, and 10 mm.

According to an embodiment of the present disclosure, a viewing-direction angle of the system may be 0°, 30°, 45°, or 70° or more. According to an embodiment of the present disclosure, a distance from the object lens module to the eye lens module may be of any length.

According to an embodiment of the present disclosure, an endoscope is provided, which includes the endoscope optical system as described above, or an endoscope optical system designed by the design method as described above. According to an embodiment of the present disclosure, the endoscope is a rigid endoscope.

According to an embodiment of the present disclosure, a method for manufacturing an endoscope is provided, which includes the following steps: providing an object lens module, a relay module, an eye lens module, an optical interface light path module, and an imaging device along a light path direction; setting an exit pupil diameter of the eye lens module or an entrance pupil diameter of the object lens module to increase a relative aperture of the system; and adjusting one or more of the object lens module, the relay module, the eye lens module, and the optical interface light path module so that an area to be observed forms a high-definition image on an imaging surface of the imaging device.

According to an embodiment of the present disclosure, the resolution of the high-definition image is MTF>0.2@40 lp/mm or more, MTF>0.2@50 lp/mm or more, MTF>0.2@60 lp/mm or more, MTF>0.2@70 lp/mm or more, MTF>0.2@80 lp/mm or more, MTF>0.2@90 lp/mm or more, MTF>0.2@100 lp/mm or more, MTF>0.2@110 lp/mm or more, MTF>0.2@120 lp/mm or more, MTF>0.2@130 lp/mm or more, MTF>0.2@140 lp/mm or more, or MTF>0.2@150 lp/mm or more.

According to an embodiment of the present disclosure, a method for manufacturing an endoscope optical system is provided, which includes providing an object lens module, a relay module, and an eye lens module along a light path direction, providing parameters of an optical interface light path module and an imaging device that are adapted to the optical system, setting an exit pupil diameter of the eye lens module or an entrance pupil diameter of the object lens module to increase a relative aperture of the system, and adjusting one or more of the object lens module, the relay module, and the eye lens module so that an image formed by an area to be observed after passing through the object lens module can form a high-definition image on an imaging surface of the imaging device defined by the parameters of the adapted optical interface light path module and the imaging device after being emitted from the relay module and the eye lens module.

According to an embodiment of the present disclosure, the resolution of the high-definition image is MTF>0.2@40 lp/mm or more, MTF>0.2@50 lp/mm or more, MTF>0.2@60 lp/mm or more, MTF>0.2@70 lp/mm or more, MTF>0.2@80 lp/mm or more, MTF>0.2@90 lp/mm or more, MTF>0.2@100 lp/mm or more, MTF>0.2@ 110 lp/mm or more, MTF>0.2@120 lp/mm or more, MTF>0.2@130 lp/mm or more, MTF>0.2@140 lp/mm or more, or MTF>0.2@150 lp/mm or more.

According to an embodiment of the present disclosure, an optical interface light path module for an endoscope optical system is provided, which includes a plurality of lenses, wherein the plurality of lenses receive light emitted, in a form of non-parallel light/divergent light after passing through a relay module and an eyes lens module, from an image formed by an area to be observed after passing through an object lens module, and emit light to form a high-definition image on an imaging surface of an imaging device.

According to an embodiment of the present disclosure, the resolution of the high-definition image is MTF>0.2@40 lp/mm or more, MTF>0.2@50 lp/mm or more, MTF>0.2@60 lp/mm or more, MTF>0.2@70 lp/mm or more, MTF>0.2@80 lp/mm or more, MTF>0.2@90 lp/mm or more, MTF>0.2@100 lp/mm or more, MTF>0.2@ 110 lp/mm or more, MTF>0.2@120 lp/mm or more, MTF>0.2@130 lp/mm or more, MTF>0.2@140 lp/mm or more, or MTF>0.2@150 lp/mm or more.

The endoscope optical system and endoscope of the present disclosure change the system resolution of the light path by increasing the overall relative aperture of the system, and this design scheme for increasing the relative aperture can be applied not only to a 30° and φ10 mm laparoscope, but also to various appearance diameters such as φ1.9 mm, φ2.7 mm, φ4 mm, φ5 mm, φ6 mm, φ8 mm, and φ10 mm, various endoscope lengths, and various viewing-direction angles, such as 0°, 30°, 45°, and 70°, without being limited to the diameter specifications, length specifications, and viewing-direction angle specifications listed above. For example, they may also be applied to a 0° or 30° laparoscope, a hysteroscope of a diameter of 10 mm, 5 mm or 4 mm, a cystoscope, an arthroscope, a nasal endoscope, a laryngoscope, an otoscope, an intervertebral endoscope, and other rigid endoscopes. The endoscope of the present disclosure may also be used in the industrial field.

The above embodiments are only for the purpose of illustrating the present disclosure, rather than limiting the present disclosure. Those skilled in the relevant technical field may make various changes and modifications without departing from the scope of the present disclosure. Equivalent technical solutions should also belong to the scope of the present disclosure.

What is claimed is:

1. An endoscope system, comprising an object lens module, a relay module, an eye lens module, an optical interface light path module, and a digital ultra-high-definition camera, which are sequentially arranged along a light path direction, wherein, during design of the endoscope system, an image for an object at a viewing distance formed by the object lens module is projected to the optical interface light path module in a form of non-parallel light after passing through the relay module and the eye lens module, and an exit pupil of the eye lens module is used as an entrance pupil of the optical interface light path module.

2. The endoscope system according to claim 1, wherein the endoscope is a rigid endoscope.

3. The endoscope system according to claim 1, wherein the non-parallel light forms a high-definition image on the digital ultra-high-definition camera after passing through the optical interface light path module.

4. The endoscope system according to claim 3, wherein an imaging quality of the image formed on the digital ultra-high-definition camera is better than an imaging quality of an image output by the optical interface light path module.

5. The endoscope system according to claim 3, wherein an imaging quality of the image formed on the digital ultra-high-definition camera is better than an imaging quality of an image formed on a visual plane of the eye lens module.

6. The endoscope system according to claim 1, wherein a relative aperture of the system is W=D/f, where W is the relative aperture, D is an entrance pupil diameter of the entire system, i.e., an entrance pupil diameter of a visual system, and f is a combined focal length of the system; $f=(f_o \cdot f_C)/f_e$, where $f_o$ is a focal length of the object lens module, $f_C$ is a focal length of the optical interface light path module, and $f_e$ is a focal length of the eye lens.

7. The endoscope system according to claim 6, wherein the relative aperture of the system of ⅙ to ¼.

8. The endoscope system according to claim 1, wherein an entrance pupil diameter of the object lens module for products of different specifications is 0.2 mm to 1 mm.

9. The endoscope system according to claim 1, wherein an exit pupil diameter of the eye lens module is 3 mm-6 mm.

10. The endoscope system according to claim 1, wherein an entrance pupil diameter of the object lens module is 0.2 mm to 1 mm, and an exit pupil diameter of the eye lens module is 3 mm to 6 mm.

11. The endoscope system according to claim 1, wherein the system is used for an aspherical endoscope.

12. The endoscope system according to claim 1, wherein the system is used for an endoscope having an appearance diameter that is one of 1.9 mm, 2.7 mm, 4 mm, 5 mm, 6 mm, 8 mm and 10 mm.

13. The endoscope system according to claim 1, wherein a viewing-direction angle of the system may be 0°, 30°, 45°, or 700 or more.

14. An endoscope for the endoscope system according to claim 1, wherein the endoscope comprises the object lens module, the relay module, and the eye lens module.

15. An endoscope for the endoscope system according to claim 1, wherein the endoscope comprises the object lens module, the relay module, the eye lens module and the optical interface light path module.

16. An optical adaptation interface for the endoscope system according to claim 1, wherein the optical adaptation interface comprises the optical interface light path module.

17. An integrated design method for an endoscope camera optical system, comprising designing the endoscope camera optical system having an object lens module, a relay module, an eye lens module, an optical interface light path module, and a digital ultra-high-definition camera, which are sequentially arranged along a light path direction; an exit pupil diameter of the eye lens module is 3 mm-6 mm and an entrance pupil diameter of the object lens module is increased to 0.2 mm to 1 mm so that a resolution of an image formed on the digital ultra-high-definition camera is improved to a modulation transfer function (MTF) >0.2@120 lp/mm.

18. The integrated design method according to claim 17, wherein at the same time the exit pupil diameter of the eye lens module is increased to 3 mm-6 mm, the entrance pupil diameter of the object lens module is increased to 0.2 mm-1 mm.

19. The integrated design method according to claim 17, wherein a relative aperture of the system is W=D/f, where W is the relative aperture, D is an entrance pupil diameter of the entire system, i.e., an entrance pupil diameter of a visual system, and f is a combined focal length of the system; $f=(f_o \cdot f_C)/f_e$, where $f_o$ is a focal length of the object lens module, fc is a focal length of the optical interface light path module, and $f_e$ is a focal length of the eye lens.

20. The integrated design method according to claim 19, wherein the relative aperture of the system of ⅙ to ¼.

21. The integrated design method according to claim 17, wherein the design method is used for a rigid endoscope.

22. The integrated design method according to according to claim 17, wherein the design method is used for an aspherical endoscope.

23. The integrated design method according to according to claim 17, wherein the endoscope camera optical system is used for an endoscope having an appearance diameter of 1.9 mm, 2.7 mm, 4 mm, 5 mm, 6 mm, 8 mm and 10 mm.

24. The integrated design method according to according to claim 17, wherein a viewing-direction angle of the endoscope camera optical system may be 0°, 30°, 45°, or 700 or more.

* * * * *